United States Patent [19]
Klatzmann et al.

[11] Patent Number: 5,843,432
[45] Date of Patent: Dec. 1, 1998

[54] RETROVIRAL VECTORS FOR THE TREATMENT OF TUMORS, AND CELL LINES CONTAINING THEM

[75] Inventors: David Klatzmann; Manuel Caruso, both of Paris, France

[73] Assignee: Universite Pierre Et Marie Curie (Paris VI), Paris, France

[21] Appl. No.: 454,385

[22] PCT Filed: Dec. 16, 1993

[86] PCT No.: PCT/FR93/01259

§ 371 Date: Oct. 11, 1995

§ 102(e) Date: Oct. 11, 1995

[87] PCT Pub. No.: WO94/13824

PCT Pub. Date: Jul. 23, 1994

[30] Foreign Application Priority Data

Dec. 16, 1992 [FR] France .................................. 92 15195

[51] Int. Cl.[6] .................................. A61K 48/00
[52] U.S. Cl. .................................. 424/93.21; 424/93.21; 435/325; 435/320.1; 435/172.3; 435/69.1
[58] Field of Search .................. 514/44; 424/93.21; 435/320.1, 172.3, 69.1, 325; 519/99; 429/93.21; 935/62, 71, 33, 55, 57, 70

[56] References Cited

U.S. PATENT DOCUMENTS 5,529,774  6/1996  Barba et al. ........................ 424/93.21

OTHER PUBLICATIONS

Ledley, F.D. Clinicla considerations in the design of protocols for somatic gene therapy. Human Gene Therapy 2:77–83, 1991.

Plautz, G. et al. Selective eliminatin of recombinant genes in vivo with a suicide retroviral vector. New Biologist 3:709–715, 1991.

Caruso et al., Proc. Natl. Acad. Sci. USA, 90, pp. 7024–7028 (1993).

Culver et al., Science, 256, No. 5063, pp. 1550–1551 (1992).

Mastrangelo et al., Seminalr in Oncology, vol. 23, 1: 4–21 1996.

Jain, Scientific Amercian, vol. 27, No:1 pp. 58–65, 1994.

Gunzburg et al., Molecular Medicine Today, vol.1 No.9, pp. 410–417, 1995.

Crystal, Science, vol. 270, pp. 404–410, 1995.

Connors, Gene Therapy, 2, 10: 702–709, 1995.

Girboa, Seminars in Oncology, 23, 1: pp. 101–107, 1996.

Deonamain et al., Gene Therapy, 2: 235–244, 1995.

Barklis et al., Cell 47:391–399 (1986).

Jaenisch et al., Cell 24:519–529 (1981).

*Primary Examiner*—Christopher S. F. Low
*Assistant Examiner*—Dave Trong Nguyen
*Attorney, Agent, or Firm*—Birch, Stewart, Kolasch & Birch, LLP

[57] ABSTRACT

The invention relates to recombinant retroviral vectors, derived from Moloney MuLV, carrying a suicide gene susceptible of transforming an inactive substance into a toxic substance for cells going through a division process, said vectors being characterized by the presence in their structure of LTR sequences from variants of MuLV, and having the properties: (a) of not being inactivated during passage through the carcino-embryonic or line germinal cells of mice; (b) the expression of the suicide gene kills only the cells in the course of division.

3 Claims, 2 Drawing Sheets

RETROVIRAL VECTORS FOR THE TREATMENT OF TUMORS, AND CELL LINES CONTAINING THEM

This application claims priority on and is the National Stage application of PCT International Application No. PCT/FR93/01259 filed on 16 Dec. 1993.

Gene therapy offers novel possibilities for the treatment of tumors.

Among the difference options, the objective of gene transfer is to kill the tumor cells either indirectly by the induction or the reinforcement of an immune response of the host (S. A. Rosenberg, Cancer Res. 51: 5074(1991) or directly by the insertion of a "suicide gene" (F. L. Moolten, Cancer Res. 46: 52–76 (1986)). The most studied suicide gene is that coding for thymidine kinase of type 1 herpès simplex virus (TK-HSV1) (G. B. Elion et al., J. Antimicrob. Chemother. 12: 9–17 (1983)). This enzyme phosphorylates nucleoside analogues such as ganciclovir (GCV). The monophosphate molecules are then converted into the triphosphate forms by cellular enzymes. The GCV triphosphate (GCV-TP) can then be incorporated into the DNA during cell division, blocking elongation and thus leading to the death of the cell. GCV-TP is thus only toxic for dividing cells.

This approach is particularly interesting for the treatment of tumors which are constituted of rapidly dividing cells in a tissue constituted of non-proliferating cells, and the expression of TK-HSV1 by the cells of a tumor situated within an organ whose cells are not dividing ought to permit the specific destruction of these cells. Furthermore, it is possible to target gene transfer into these tumor cells by using for the transduction of TK-HSV1 recombinant retroviruses whose genome can only be integrated and expressed in dividing cells.

The first experimental ablation model by GCV of tumor cells expressing TK-HSV1 was set up by Moolten (F. L. MOOLTEN, Cancer Res., 46, 1986, p. 5276–5281); F. L. MOOLTEN and J. M. WELLS, J. Natl. Cancer Inst., 82, 1990, p. 297–300). He showed an antitumor effect of GCV on the growth of tumor cells in mice after transfection of the TK-HSV1 gene in vitro, and reimplantation in the animal. Recently, the elimination of microscopic experimental cerebral tumors by stereotaxic injection of cells producing TK-HSV1 retroviruses and treatment by GCV has been reported by Culver (K. W. Culver et al., Science 256: 1550–1552 (1992)).

However, in this model the authors were unable to analze the effect of such a treatment on macroscopic established tumors which rapidly become lethal. Now, in patients solid tumors are the principal target of this type of treatment and the problem of the transduction of the suicide genese in the context of a tumoral mass is much more problematical.

In man, hepatic metastases are a frequent complication of digestive cancers. Partial hepatectomy is only possible in about 15% of cases, and other treatments such as local chemotherapy or immunotherapy have hitherto given only modest, even disappointing results. The present work shows the efficacy of the treatment of experimental hepatic metastases in the rat after in vivo transfer of the TK-HSV1 gene by direct injection of murine fibroblasts producing recombinant retroviral particles.

In this context, one of the objectives of the present invention is the development of a packaging cell-recombinant retroviral vector system utilizable in therapy to treat established tumors, in particular hepatic tumors, and in which the expression product of the recombinant gene is capable of converting a non-toxic prodrug into a drug toxic for the cells expressing said recombinant gene.

More precisely, the objective of the present invention is to construct a recombinant retroviral vector capable, after transformation of a fibroblast packaging line, of producing retroviral pseudoparticles which, after infection of dividing cells, results in the expression of the transduced gene without leading to inactivation of said vectors which occurs and has been described in particular with MuLV-Moloney.

The murine transgenic lines of the Mov series were established by Jaenisch et al. by infection of mouse embryos with the Moloney-MuLV virus before implantation (Jaenisch et al., Cell 24: 519–529 (1981)).

At this stage of development the animals are usually resistant to the infection by the MuLV, the hypothesis being that the proviral DNA undergoes a process of methylation acquired during successive cell divisions and this methylation prevents the transcription of the DNA.

However, with some Mov lines, the MuLV genome may be reactivated at a particular stage of development and the rodents develop leukemias induced by this oncogenic virus. This is the case for the following three lines: Mov3, Mov9 and Mov13.

This phenotype might be due to mutations in the LTR.

IN THE FIGURES

Figure 1:
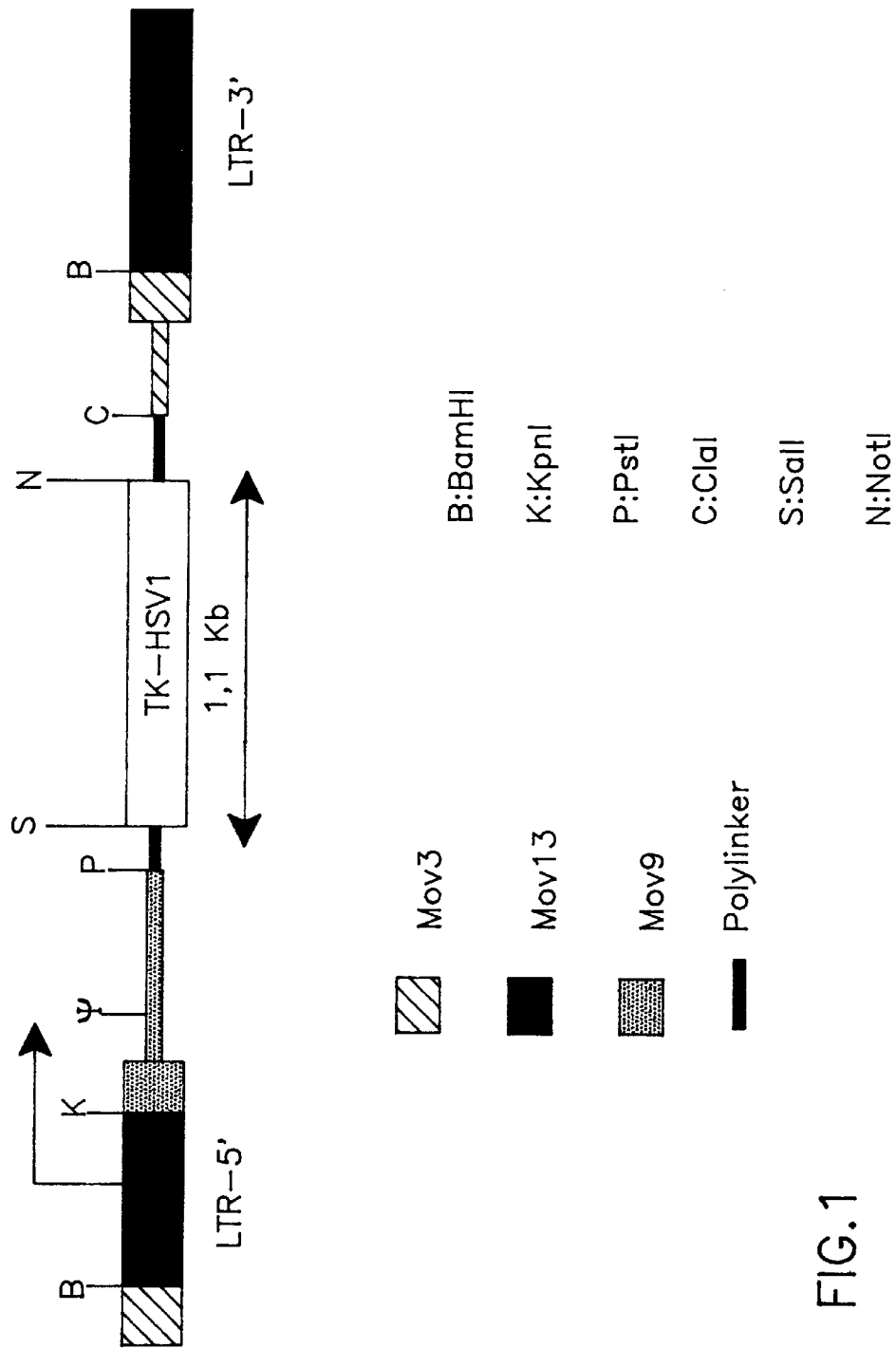
FIG. 1 depicts the structure of the recombinant retroviral vector pMTK.

Hence, the object of the present invention is the construction of a recombinant retroviral vector derived from the MuLV-Moloney carrier of a suicide gene capable of converting an inactive substance into a substance toxic for dividing cells, and characterized in its structure by the presence of LTR sequences derived from such variants of the MuLV which have the property of not being inactivated during passage through mouse carcino-embryonic or germ line cells and capable of transfecting cells which divide, in particular tumor cells.

The suicide gene used is the thymidine kinase gene of the herpès simplex virus.

The invention also relates to packaging lines transfected by this recombinant vector derived from the Moloney retrovirus and comprising the TK-HSV1.

The invention relates more particularly to the M11 line deposited with the C.N.C.M. on 15 Dec. 1992 under the number No. I-1278.

The in situ administration into a hepatic tumor of transfected lines carrying a TK-HSV1 gene followed by a treatment by a nucleoside analogue such as ganciclovir leads to a reduction of the tumor mass by more than 90% under the experimental conditions described below (cf. FIG. 2).

Finally, the invention relates to therapeutic compositions containing the cell line transfected by recombinant retroviruses, utilizable in combination with a prodrug to lead to selective destruction of the tumor cells.

The invention takes advantage of three separate phenomena:

1) the injection of the composition into dividing cells, themselves surrounded by quiescent cells;
2) the presence in this composition of recombinant retroviral vectors which only infect dividing cells, and consequently the gene is expressed only in these cells;

3) the expression of the suicide gene only kills dividing cells. p In other words, all of the dividing cells infected by the recombinant retroviruses, and expressing the TK-HSV1 gene are capable of being killed after treatment with the nucleoside analogue which may thus be converted into a nucleoside triphosphate and stops the elongation of the DNA after its incorporation into the growing DNA chain.

The vulnerable cells in this phenomenon are thus the target tumor cells; and the transfected fibroblasts of the composition of the invention.

The objective of the experimental conditions given below is to illustrate the construction of the retroviral vector which makes possible the selectivity of the "killer" effect described above, the preparation of the lines transfected by such a vector and the therapeutic efficacy of the composition containing these lines when the treatment is combined with the administration of a prodrug such as ganciclovir.

1) Construction of the retroviral vector pMTK

The construction of a vector is described in which the TK-HSV1 gene has been placed under the control of a 5' LTR of the mutant MuLV strains Mov3, Mov13 and Mov9.

The use of this plasmid for the transfection of CRIP fibroblast cells is described subsequently.

The ligations of the different restriction fragments of the strains Mov3, Mov13 and Mov9 were carried out in the following manner:

5'-LTR

Mov3 up to the BamHI site (−350 from the transcription start).

Mov13 from the BamHI site (−350) up to the KpnI site (+30).

Mov9 from the KpnI site (+30) up to the PstI site (+560) (contains the packaging sequence).

The non-coding sequence at the 3' of the ClaI site (+7674) up to U3) (+7817 is derived from Mov3.

3'-LTR

Mov3 up to the BamHI site situated at position 7910 (or −350).

Mov13 up to the end of U5.

The 1100 base pairs fragment containing the TK-HSV1 gene and defined by the SalI and NotI ends was inserted into the polyliner at the sites indicated in FIG. 1.

All of these cloning operations were carried out using standard procedures (Maniatis et al. (1982), Molecular Cloning, a laboratory manual).

FIG. 1 presents the recombinant retroviral vector.

2) Cell cultures and transfection, establishment of the packaging line M11:

The Ψ CRIP fibroblast cells (O. DANOS et al., Proc. Natl. Acad. Sci. USA, (1988), 85: 6460–64) were cotransfected with the retroviral vector pMTK (20 µg) expressing TK-HSV1 under the control of the LTR and a selection plasmid (1 µg) (pWLNeo, Stratagene). Several clones were isolated by G418 selection. The production of viral particles by these clones were then tested by infection of TK-L cells and selection of cells on HAT. The infection was carried out with serial dilutions of the supernatant containing the viral particles, and counting the number of colonies obtained under these conditions enables the infectious titer to be determined. The selected clone M11 possesses a titer of $5 \times 10^5$ viral particles/ml. The line NB16 (N. FERRY et al., Proc. Natl. Acad. Sci. (1991) 88: 8377–81), also derived from Ψ CRIP cells, was used to evaluate the infection of the tumor cells. It produces viral particles expressing the nls-LacZ gene with with an infectious titer of $10^4$ viral particles/ml.

The DHDK12 line is a cell line established from chemically induced colon cancer in the rate BDIX described in Martin et al., Virchows Archiv. A. Pathol. Anat. (1991) 418: 193.

The invention also relates to the populations of fibroblast cells transformed by a recombinant retroviral vector carrying the suicide gene.

3) Therapeutic protocol

Syngenic male BDIX rats were used. An isolated liver tumor was induced by direct injection of the DHDK12 cells under the capsule of the liver. On day 5 the liver tumors had a diameter included between 2 and 3 mm and contained approximately 150 million cells.

At this time, the rats received an intra-tumoral injection of the fibroblasts producing recombinant retroviruses ($20 \times 10^6$ cells).

The animals of the control group received NB16 fibroblast cells which produced a recombinant retrovirus expressing the nls-lacZ gene. This gene codes for a beta-galactosidase with a localization signal in the nucleus and can thus serve as an indicator gene to monitor the infection of the tumor cells in vivo. The NB16 clone produces the virus with a titer of $10^4$ plaque-forming units per milliliter. The group of treated animals were infected with the M11 line which produced $5 \times 10^5$ infectious particles per milliliter.

After the intra-tumoral injection of the packaging cells, the animals were left for a period of 5 days in order that the infection of the tumor cells by the recombinant retrovirus may occur.

Five days later, i.e., on day 10, all the rats received ganciclovir (GCV) (Syntex) for five days at a dose of 150 mg/kg twice a day by the intraperitoneal route. The rats were then sacrificed at the end of the treatment with ganciclovir, i.e., 15 days after the first injection and an autopsy was performed comprising the measurement of the size of the tumors and a pathological anatomy study.

Figure 2:
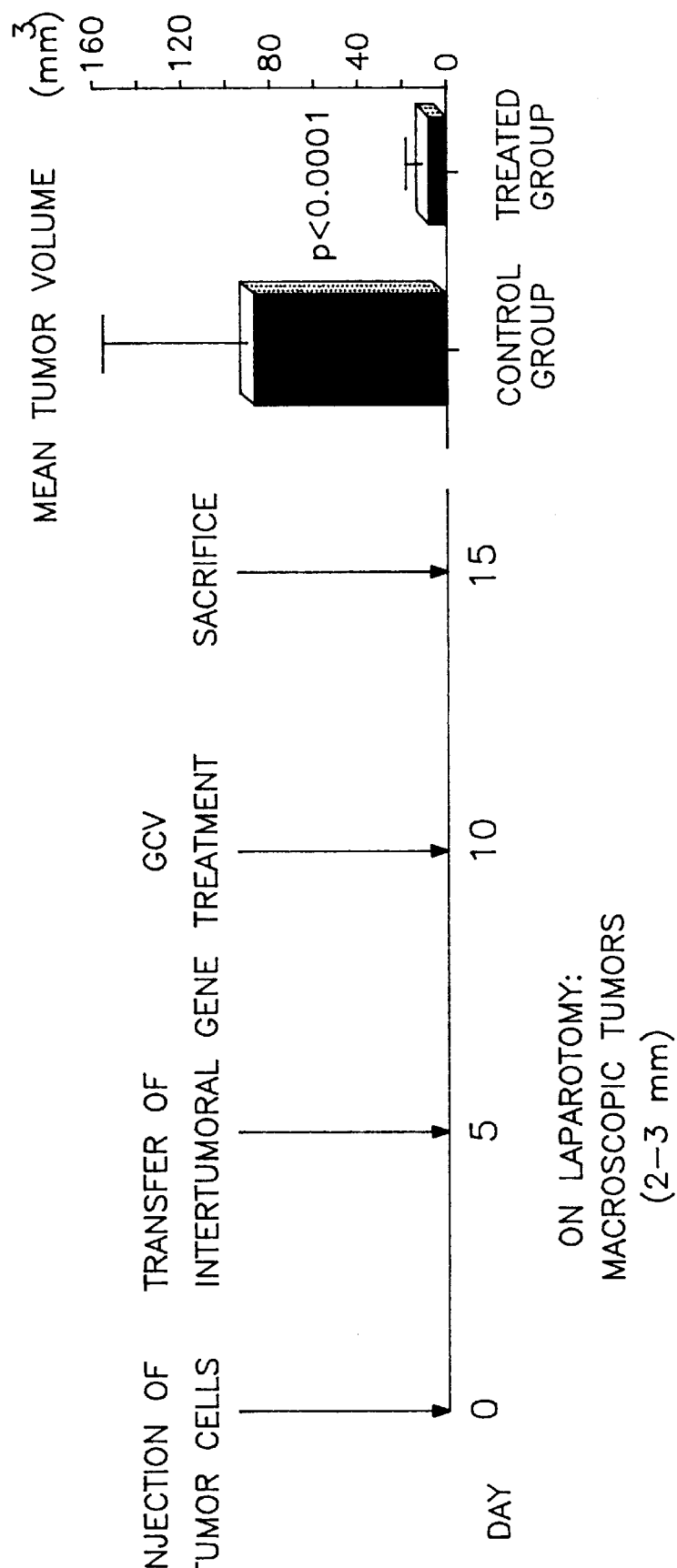
FIG. 2 shows the results of experiments on in situ administration into a hepatic tumor of transfected lines carrying a Tk-HSV1 gene followed by treatment with a nucleoside analogue.

FIG. 2 summarizes the experimental protocol described above and the results obtained on the reduction of the tumors described below.

RESULTS

Control group (number of rats: 12):

On autopsy, all of the injected lobes showed macroscopic tumors, the mean maximal diameter of which was 6.5±2.1 mm (extremes: 3 and 10 mm). Their volume is calculated according to the formula $V = A \times B^2/2$, in which A is the maximal diameter, and B is the smallest diameter measured at the largest cross-section of the tumor (G. Carlsson et al., 1983), J. Cancer Res. Clin. Oncol. 105: 20). The volume calculated under these conditions was 86.3±65.1 mm$^3$ (mean±S.D.).

The pathological examination of the tumors revealed a typical appearance of a poorly differentiated adenocarcinoma, consisting essentially of tumor cells organized in lobules of variable thicknesses. The stroma appeared fibrotic and surrounded with mononuclear inflammatory cells. The percentage of tumor cells in the tumor was estimated at 60%.

The nuclear beta-galactosidase activity is detected in Xdale-stained cryostatic sections in the 6 control livers analyzed. The fraction of infected tumor cells was less than 1%.

Treated group (number of rats: 13):

The mean diameter of the tumors was 3±1.1 millimeters (extremes: 0.5 and 4 mm) and the volume was 8.1±6.7 mm$^3$ (P<0.0001, Mann and Whitney test) (FIG. 2). The pathological examination of the tumors revealed the efficacy of this treatment by a very considerable dimunution in the size of the tumors. Of the 11 livers analyzed (2 were used for the lacZ analytical control), two had tumors showing a reduction of 60 to 20% of the tumor cells. These cells were poorly organized and necrotic. They were grouped together in a fibrotic reaction surrounding inflammatory mononuclear cells and a cancerous hyperplasia. In 5 other livers less than 10% of cancer cells could be detected, with a massive fibrotic reaction. In the last four livers, a few rare cancer cells were seen and a massive necrosis of the tumor surrounded by a fibrotic reaction was observed.

In all of these rats, there were signs of a parenchymatous regeneration.

These studies show a regression of established tumors after in vivo transfer of a suicide gene.

In patients a precise targetting of the injection of the transformed packaging fibroblasts into the tumor mass can be facilitated by ultrasonic assistance or with the aid of any microprobe whose function is the localization of said tumoral masses.

Knowing that the level of infected cells expressing the TK-HSV1 gene was less than 10% and that the tumor is reduced by more than 90% after addition of ganciclovir, it may be supposed that the phenomenon of "metabolic cooperation", already described by Moolten (Moolten, 1986) or the "proximity effect" (Culver, 1992) is also effective in the case of a large tumor mass. This phenomenon could be explained by the transfer of the phosphorylated ganciclovir from the cells expressing the TK-HSV1 gene to the cells not expressing it.

The use of the packaging fibroblast cells, transformed by a recombinant retroviral vector carrying a suicide gene as medicine combined with a treatment with ganciclovir seems to be efficacious for the reduction of tumoral masses and the treatment of established cancers.

The invention is not limited to the embodiment which has been illustrated above, in particular to the use of the TK-HSV1/ganciclovir couple. The specialist skilled in the art is able to imagine other active couples which may be used for the same purpose. As a killer gene mention should be made, for example, of the thymidine kinase gene of the cytomegalovirus coupled to ganciclovir. The gene sequence and the structure of the protein of this thymidine kinase show that the latter is quite different from the cellular kinases or the kinase of the herpès simplex 1 virus. Mention may also be made of a bacterial enzyme, cytosine deaminase, which is capable of converting 5-fluorocytidine into a toxic nucleotide analogue 5-fluorouracil. Finally it is possible to image any other system of condition toxicity based on an enzyme-drug couple and which, as a result of the system described above, enables dividing cells to be killed specifically.

We claim:

1. A genetically altered Moloney MuLV retroviral vector comprising:
   (a) a suicide gene comprising the herpes simplex virus thymidine kinase gene (HSV-tK); and
   (b) Mov3, Mov9 and Mov13 LTR sequences;
   wherein said genetically altered Moloney MuLV retroviral vector is not inactivated by passage through mouse carcinoembryonic or germ cell lines.

2. A fibroblast packaging cell line transformed with the retroviral vector of claim 1.

3. A method for killing solid tumor cells, said method comprising the steps of:
   (a) injecting into a solid tumor a fibroblast packaging cell line transformed with a genetically altered Moloney MuLV retroviral vector comprising:
      (i) the herpes simplex virus thymidine kinase gene (HSV-tK);
      (ii) Mov3, Mov9 and Mov13 LTR sequences; wherein said genetically altered Moloney MuLV retroviral vector is not inactivated by passage through mouse carcinoembryonic or germ cell lines;
   and thus transferring the retroviral vector which expresses the HSV-tK gene into the tumor cells; and
   (b) killing the tumor cells in said solid tumor by administering to the solid tumor a prodrug that is converted by the thymidine kinase expressed from the HSV-tK gene of step (a), said prodrug is converted by said thymidine kinase to a toxic product that kills the tumor cells.

* * * * *